United States Patent [19]
Irie

[11] Patent Number: 5,895,411
[45] Date of Patent: *Apr. 20, 1999

[54] EMBOLIZING SYSTEM

[75] Inventor: Toshiyuki Irie, Tokorozawa, Japan

[73] Assignee: SciMed Life Systems Inc., Maple Grove, Minn.

[*] Notice: This patent issued on a continued prosecution application filed under 37 CFR 1.53(d), and is subject to the twenty year patent term provisions of 35 U.S.C. 154(a)(2).

[21] Appl. No.: 08/858,519

[22] Filed: May 19, 1997

Related U.S. Application Data

[63] Continuation of application No. 08/378,808, Jan. 27, 1995, abandoned.

[51] Int. Cl.$^6$ ............................................. A61B 17/08
[52] U.S. Cl. ............................. 606/213; 606/108; 606/151
[58] Field of Search ............................. 606/1, 108, 151, 606/159, 190–200, 213

[56] References Cited

U.S. PATENT DOCUMENTS

| | | | |
|---|---|---|---|
| 3,921,632 | 11/1975 | Bardani . | |
| 4,708,718 | 11/1987 | Daniels | 604/53 |
| 4,900,303 | 2/1990 | Lemelson | 604/54 |
| 4,994,069 | 2/1991 | Ritchart et al. | 606/191 |
| 5,108,407 | 4/1992 | Geremia et al. | 606/108 |
| 5,167,624 | 12/1992 | Butler et al. | 604/60 |
| 5,181,921 | 1/1993 | Makita et al. | 606/195 |
| 5,226,911 | 7/1993 | Chee et al. | 606/191 |
| 5,234,437 | 8/1993 | Sepetka | 606/108 |
| 5,250,071 | 10/1993 | Palermo | 606/108 |
| 5,256,146 | 10/1993 | Ensminger et al. | 604/104 |
| 5,261,916 | 11/1993 | Engelson | 606/108 |
| 5,263,964 | 11/1993 | Purdy | 606/200 |
| 5,290,310 | 3/1994 | Makower et al. | 606/108 |
| 5,292,332 | 3/1994 | Lee | 606/213 |
| 5,304,195 | 4/1994 | Twyford, Jr. et al. | 606/191 |
| 5,312,415 | 5/1994 | Palermo | 606/108 |
| 5,320,639 | 6/1994 | Rudnick | 606/213 |
| 5,324,306 | 6/1994 | Makower et al. | 606/213 |
| 5,334,216 | 8/1994 | Vidal et al. | 606/151 |
| 5,342,394 | 8/1994 | Matsuno et al. | 606/213 |
| 5,350,397 | 9/1994 | Palermo et al. | 606/200 |
| 5,354,295 | 10/1994 | Guglielmi et al. | 606/32 |

FOREIGN PATENT DOCUMENTS

| | | |
|---|---|---|
| 2 641 692 | 1/1989 | France . |
| 233 303 A1 | 2/1986 | Germany . |
| WO 94/06503 | 3/1994 | WIPO . |

OTHER PUBLICATIONS

*Catheters, Embolic Agents Spark Neurointervention*, by Gary Duckwiler, M.D. and Jacques Dion, M.D., "Diagnostic Imaging", May 1994, pp. 66–72.

*Interventional Neuroradiology*, by Joseph M. Eskridge, M.D., "Radiology", Sep. 1989, pp. 991–1006.

*Primary Examiner*—Glenn K. Dawson
*Attorney, Agent, or Firm*—Westman, Champlin & Kelly, P.A.

[57] ABSTRACT

An embolizing system includes a catheter having a lumen, an elongate member, insertable within the lumen of the catheter, and an occlusion particle. The occlusion particle has a receiving passageway therein for receiving the elongate member so the elongate member guides movement of the occlusion particle.

10 Claims, 4 Drawing Sheets

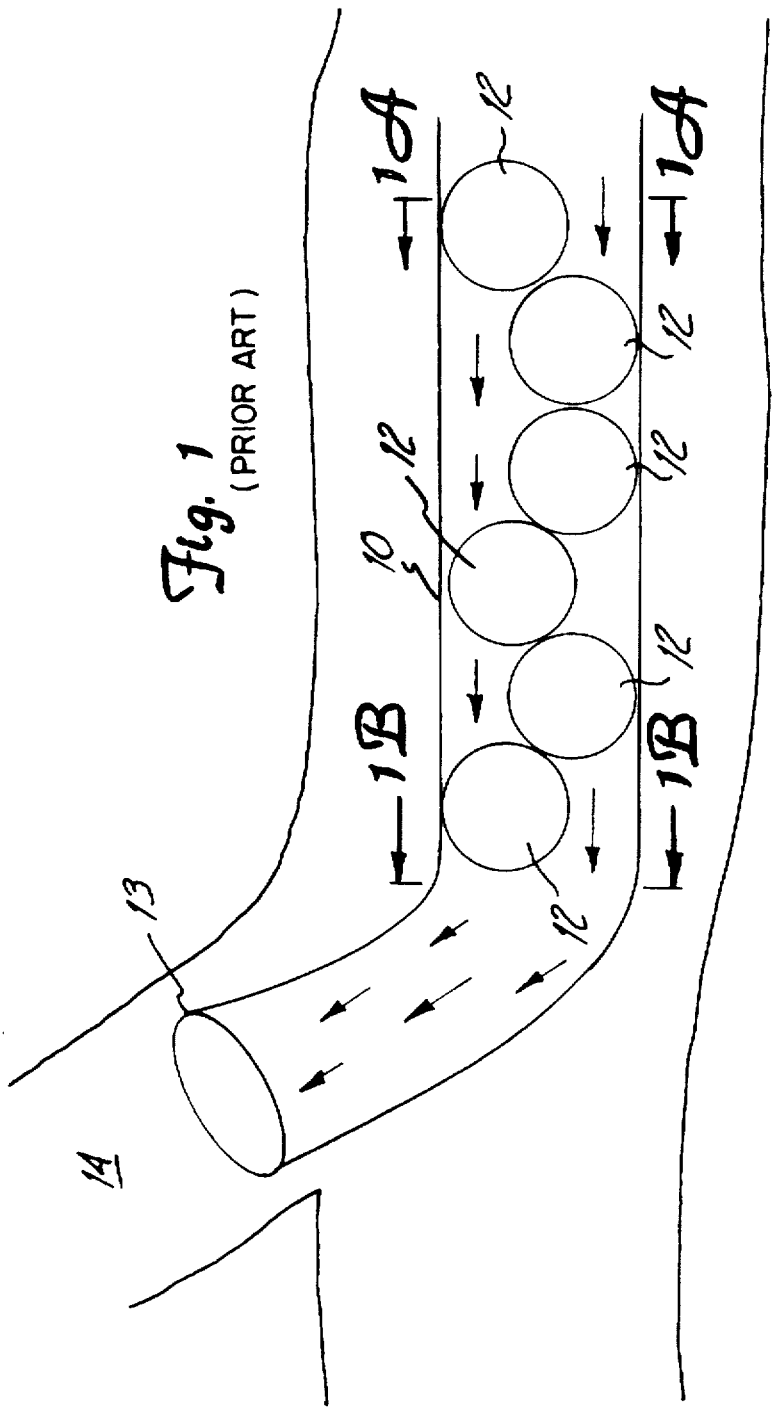

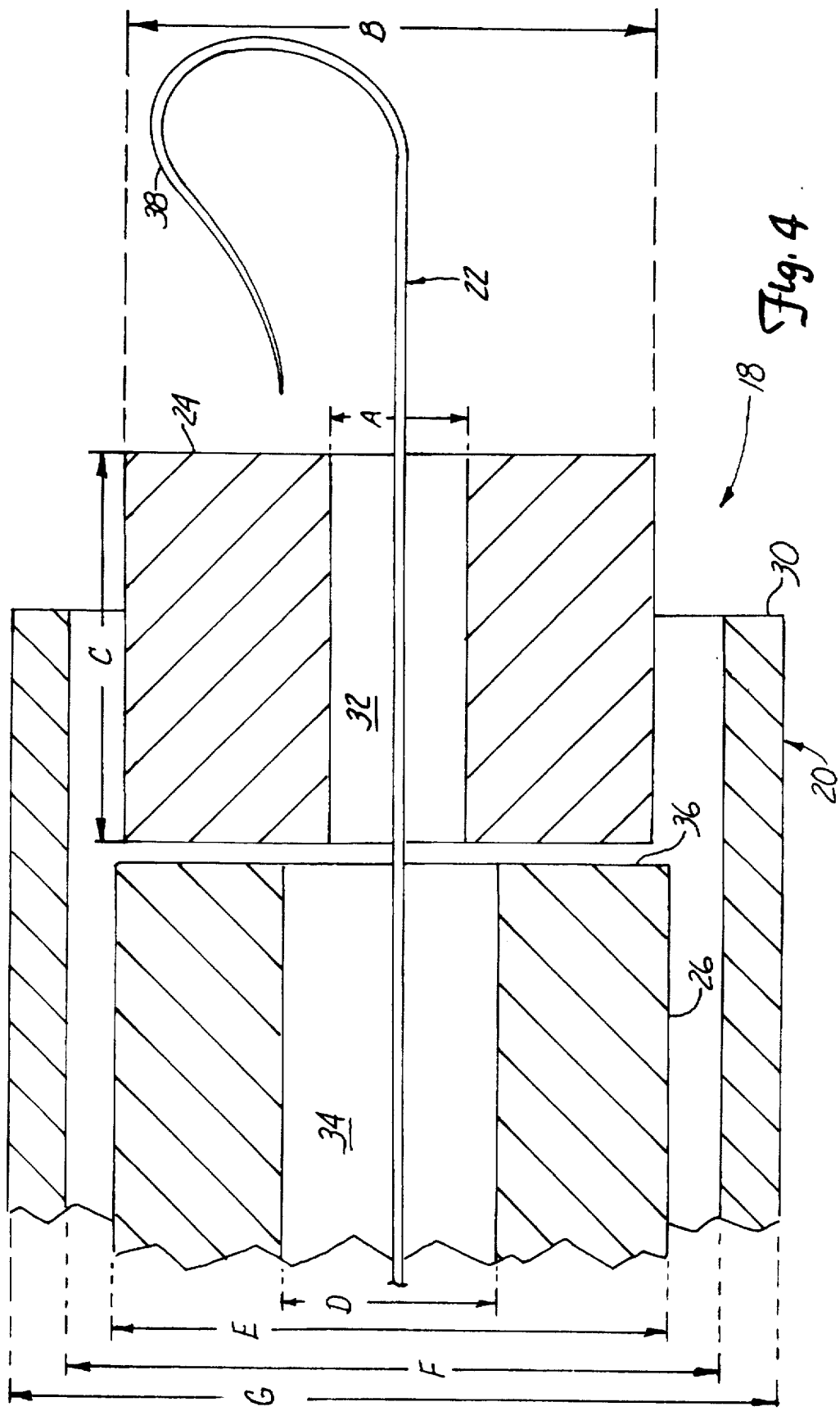

EMBOLIZING SYSTEM

This is a continuation of application Ser. No. 08/378,808, filed Jan. 27, 1995, now abandoned.

BACKGROUND OF THE INVENTION

The present invention relates to an embolization system to block flow through a selected portion of a lumen. More particularly, the present invention relates to a system for introducing occlusion particles into the lumen of a blood vessel.

Embolization techniques are currently used to treat a variety of vascular and non-vascular diseases. Such diseases include arteriovenous malformations (AVMs), aneurysms, arteriovenous fistulas, and tumors. There are currently three basic types of embolization systems in use. Those systems include embolic liquids, solid or solid-type agents, and particles.

Embolic liquids include glues, (polymerizing agents), alcohols, and precipitating agents. Typical examples of embolic liquids are n-butylcyanoacrylate (n-BCA), ethyl alcohol and a precipitating agent sold by Ethicon of Germany under the tradename Ethibloc. The glues used as embolic liquids typically act to polymerize and harden in the vessel, thereby blocking or occluding the vessel into which they are introduced. The alcohol or alcohol derivatives cause tissue damage to the vessel with resulting thrombus formation for occlusion. Precipitating agents typically include a precipitating agent which is dissolved in infusion solution, but insoluble in a blood environment. When the infusion solution is introduced into the vessel, the precipitating agent precipitates out to cause occlusion.

Embolic liquids currently suffer from a number of disadvantages. One disadvantage is that the liquids lack radiopacity. This makes it difficult to monitor the administration of the embolic liquids. Another disadvantage is that the release of embolic liquids into the vessel to be occluded is difficult to control. The liquids must be released upstream of the site at which eventual occlusion is desired. Blood flow carries the embolizing liquid through the lumen of the vessel, and it is difficult to control the release of a proper amount of occlusive liquid into the vessel to insure that occlusion occurs at the desired site in the vessel.

Solid agents, when used in an embolization system, conventionally include occluding articles which are more discrete in nature than embolic liquids. Such articles have typically been formed of suture material or coils which are introduced into the vessel. The suture material (often silk), once released, assumes a convoluted shape within the vessel to cause thrombus formation and occlusion. A suture material occlusion system is discussed in the Ritchart et al. U.S. Pat. No. 4,994,069 issued Feb. 19, 1991. Coils, or coil assemblies, used as solid occlusion agents are shown in the Sepetka U.S. Pat. No. 5,234,437 issued Aug. 10, 1993. The coils occlude the desired site in the vessel by posing a physical barrier to blood flow. This promotes thrombus formation at the desired site, which eventually occludes the vessel.

However, solid agents also suffer from a number of disadvantages. First, solid agents conventionally depend on thrombus formation in order to accomplish complete occlusion. However, if anti-coagulant agents are introduced into the bloodstream during surgery, the anticoagulant can substantially prevent thrombus formation thereby minimizing the occlusive effect of the solid agent. Additionally, the bodies' natural clot dissolving factors can cause recanalization. Further, when the solid agent is a coil, it is either an insertion coil or a detachable coil. Insertion coils are introduced into the vessel by injection, or by being pushed through a base catheter. Once introduced into the vessel, they can become irretrievable and accurate delivery is difficult to control. When the coil is detachable, it must be particularly sized to fit the lumen of the vessel at the desired occlusion site. However, the size of the lumen of the vessel is difficult to predict. Therefore, it is not uncommon for the treating physician to move the solid agent (detachable coil) to the occlusion site only to find out that the dimensions of the detachable coil are inappropriate to the occlusion site in the vessel. This requires the physician to remove essentially the entire coil system and to re-insert the system with a different size detachable coil. It may be necessary to repeat this process a number of times before the properly sized solid agent is finally inserted in the lumen. Also, when removing an improperly sized detachable coil, it is not uncommon for the coil to engage the base catheter and unravel or unwind. Such a system is time consuming and inefficient.

A third conventional embolization system utilizes what are known as embolizing particles or occlusion particles. Embolizing particles are typically smaller than solid occlusion agents and are suspended in solution. The solution is injected into the lumen to be occluded through a catheter. Typical embolization particles are made of polyvinylalcohol (PVA). The polyvinylalcohol particles are formed of a ground block of material which is put through a series of sieves to segregate the particles into various size categories. The particles are suspended in solution and injected into the vessel through a delivery catheter.

However, conventional embolizing particles also suffer from a number of disadvantages. For example, in conventional systems, the particles cannot be easily retrieved once they are injected into the vessel. In addition, it is very difficult to control precisely how much of the injectate is delivered. Further, typical PVA particles are in suspension and are therefore not typically well aligned as they travel through the catheter. Therefore, they can wedge together and substantially block the delivery catheter. This requires the treating physician to either remove the entire system, including the delivery catheter, and replace it with another system, or to take extra time to remove the blockage from the delivery catheter. Another major problem associated with injecting PVA particles to occlude a vessel is referred to as reflux. Essentially, as PVA is injected into the vessel, and as the vessel begins to close, the distal flow at the occlusion site becomes smaller. Therefore, less injectate is needed at the occlusion site. If too much solution is injected, and the distal flow cannot accommodate the extra injectate, then the flow becomes proximal and can occlude a lumen of a normal vessel at a proximal site. This problem essentially arises from the difficulty in controlling the amount of PVA particles injected into the vessel.

SUMMARY OF THE INVENTION

An embolization system includes a catheter having a lumen. An elongate member is insertable within the lumen of the catheter. An occlusion particle has a receiving passageway therein for receiving the elongate member so the elongate member guides movement of the occlusion particle through the lumen of the catheter and into a vessel.

BRIEF DESCRIPTION OF THE DRAWINGS

FIGS. 1, 1A and 1B illustrate one common problem with prior art embolization systems.

FIG. 4 is an enlarged and more detailed cross-section of the embolization system shown in FIGS. 2 and 3.

DETAILED DESCRIPTION OF THE PREFERRED EMBODIMENTS

Figure 2:
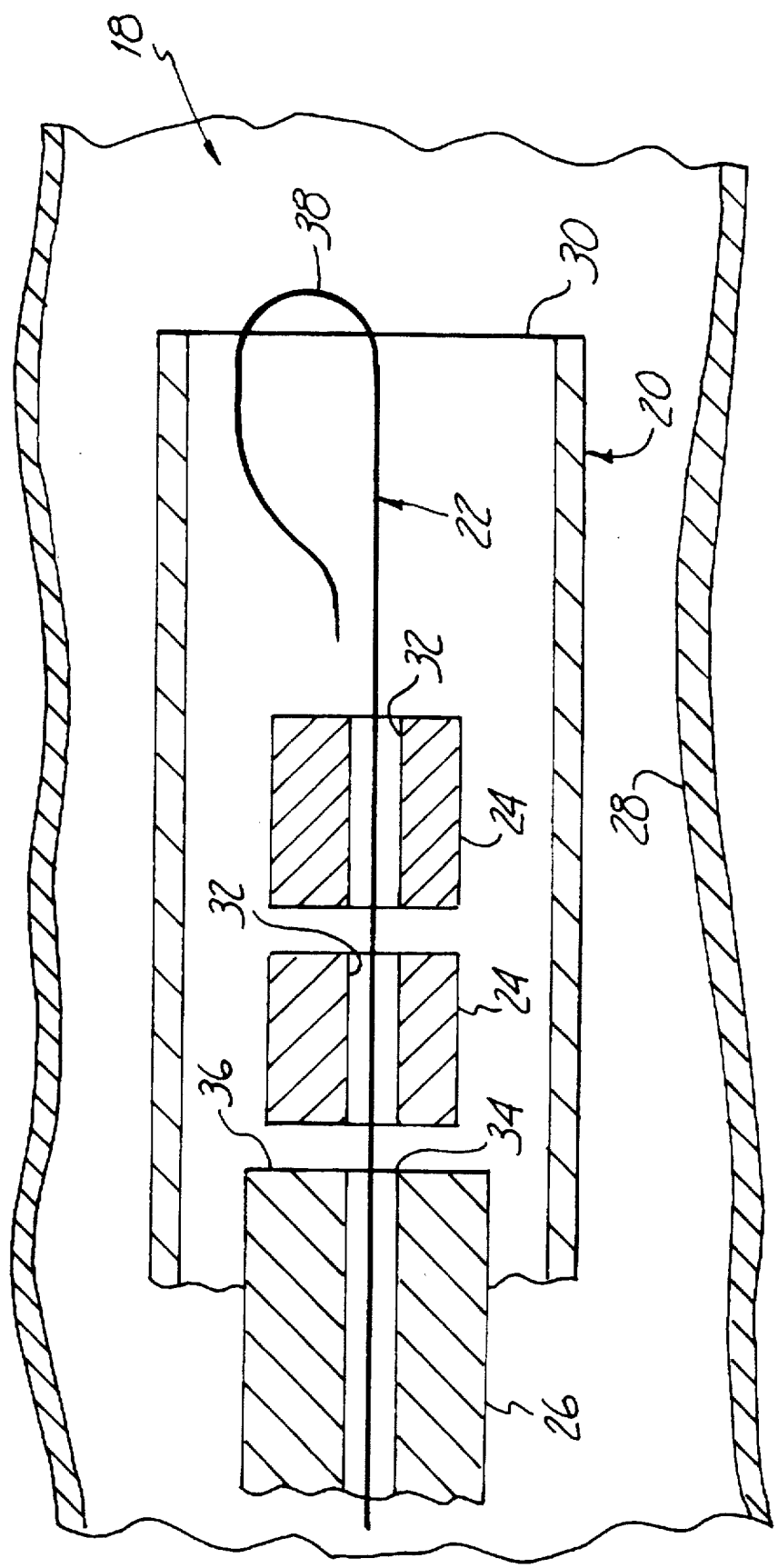
FIG. 2 is a cross-sectional view of an embolization system according to the present invention.

FIGS. 1, 1A and 1B illustrate a common problem with polyvinylalcohol (PVA) injection type embolization systems. FIG. 1 shows a delivery catheter 10 residing in a vessel 11 and having a distal end 13. Catheter 10 is carrying a PVA solution, or injectate, which includes a plurality of PVA particles 12. While PVA particles 12 are not typically perfect spheres, they are illustrated as spheres for the sake of simplicity in FIG. 1. In operation, delivery catheter 10 is typically manipulated through vessel 11 so distal end 13 is proximate a desired occlusion site 14. When distal end 13 of delivery catheter 10 reaches occlusion site 14, the solution carrying PVA particles 12 is injected into the delivery catheter 10 and delivered to occlusion site 14. It is difficult to predict the precise amount (both size of particles and number of particles required) of injectate needed to occlude vessel 11 at site 14. Also, it is difficult to precisely control the amount of injectate delivered to site 14. This results in a wide variety of problems, most of which were mentioned in the Background of the Invention portion of the present specification.

In addition, PVA-type occlusion can also suffer from one of the problems commonly associated with discrete or solid-type occlusion devices. When the PVA particles 12 are delivered to site 14, thrombus formation can cause occlusion. However, during surgery, anticoagulant therapy may be administered. This therapy can substantially prevent thrombus formation. Thus, the treating physician must inject more solution carrying PVA particles 12. Due to the difficulty in controlling delivery of an accurate amount (size and number of particles) of the solution, the need to deliver extra solution exacerbates the problem of potential reflux in vessel 11. Further, the body has natural clot dissolving factors which can begin to act on the thrombus. This can cause the thrombus at site 14 to dissolve over time.

In accessing site 14, catheter 10 must commonly make a number of bends. FIG. 1A, taken along section lines 1A—1A in FIG. 1, shows the conventional cross-section of catheter 10 as being circular. However, FIG. 1B is taken along section lines 1B—1B of FIG. 1 at a point where catheter 10 bends to access site 14. The cross-section at the bent portion of catheter 10 is oval shaped. Since particles 12 are simply mixed in solution and injected through catheter 10, they are not typically aligned along a longitudinal axis of catheter 10. As the particles reach the oval cross-section of catheter 10, it is not uncommon for the particles to lodge against one another and the walls of catheter 10 to obstruct flow of the solution through catheter 10. This requires the physician to either insert some type of device into catheter 10 to dislodge the blockage, or it requires the physician to completely remove catheter 10 and insert another delivery catheter into vessel 11. This is time consuming, cumbersome and inefficient.

FIG. 2 is a cross-sectional view of an embolization system 18 according to the present invention. Embolization system 18 includes delivery catheter 20, wire 22, occlusion particles 24, and pusher 26. Embolization system 18 is shown inserted within the lumen of a vessel 28.

In operation, delivery catheter 20 is typically inserted into vessel 28 and its distal end 30 is manipulated to access an occlusion site in vessel 28. Particles 24 each have a wire receiving passageway 32 therein. Particles 24 are mounted onto wire 22 by inserting wire 22 through the wire receiving passageway 32 in particles 24. When a sufficient number of particles 24 are loaded onto wire 22, pusher 26 is also mounted onto wire 22. In a preferred embodiment, pusher 26 is a catheter, or other tube, having a lumen 34 therein for receiving wire 22. Pusher 26 has a distal end portion 36 which engages particles 24 as pusher 26 is advanced along wire 22. Wire 22, particles 24, and pusher 26 are all advanced within delivery catheter 20 to distal end 30 of delivery catheter 20, proximate the site to be occluded.

Wire 22 has a curved portion 38 at its distal end. The curved portion 38 is illustrated in FIG. 2 is a generally J-shaped or hook-shaped portion. Curved portion 38 serves to retain particles 24 on wire 22 until the treating physician desires to release a particle 24 from wire 22.

Figure 3:
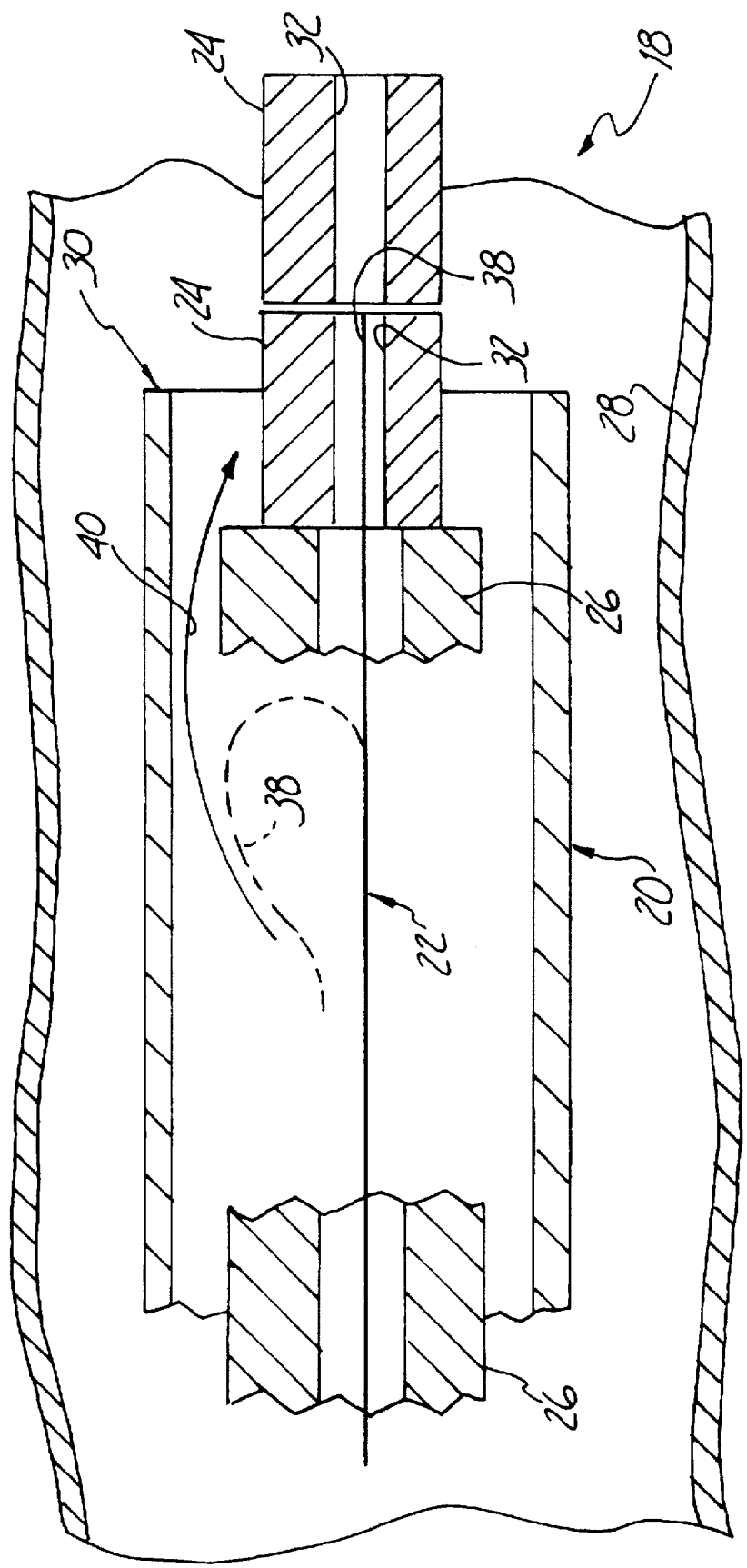
FIG. 3 is a cross-sectional view of the embolization system shown in FIG. 2, illustrating delivery of an occlusion particle into a vessel.

FIG. 3 illustrates the operation of embolization system 18 when the treating physician desires to release a particle 24 into vessel 28. When distal end 30 of delivery catheter 20 is positioned to access a desired occlusion site in vessel 28, the treating physician advances pusher 26 along wire 22 until particles 24 engage curved portion 38 at the distal end of wire 22. The treating physician then continues to advance pusher 26 over wire 22 causing the distal most particle 24 to abut curved portion 38 of wire 22.

In the preferred embodiment, wire 22 is formed of a resilient, shape-memory material, such as a super elastic metal. Wire 22 can also be another suitable elongate member such as plastic (teflon) material or other resilient synthetic or natural material. Thus, as the treating physician continues to advance pusher 26, the distal most particle 24 causes curved portion 38 of wire 22 to straighten from its curved portion shown in phantom in FIG. 3, along a path generally indicated by arrow 40, to a straightened position shown in FIG. 3. Once wire 22 is in the straightened position, the treating physician continues to advance pusher 26 until a desired number of particles 24 are released from wire 22 into vessel 28. When the treating physician has released a desired amount of particles 24 into vessel 28, the treating physician retracts pusher 26 along wire 22. This allows curved portion 38 of wire 22 to return to its original position (shown in phantom in FIG. 3). Once in its original curved position, curved portion 38 of wire 22 again serves to retain additional particles 24 on wire 22.

Particles 24 are preferably radiopaque particles, such as platinum, making them visible under fluoroscopy. This allows the physician to achieve a high degree of control in releasing a desired number of particles 24 into vessel 28. When the desired number of particles 24 have been released, the treating physician can very easily prevent additional particles 24 from being released by simply retracting pusher 26 on wire 22. Further, with the present invention, the treating physician can recover all particles 24 which are in delivery catheter 20 and which are still on wire 22. Recovering such particles is extremely difficult in prior art embolization systems in which an injectate solution is used.

FIG. 4 is an enlarged cross-sectional view of embolization system 18 according to the present invention. FIG. 4 illustrates a number of preferred dimensions for items in embolization system 18. The inner diameter of particle 24 is designated by the letter A. The outer diameter of particle 24 is designated by the letter B. The length of particle 24 is designed by the letter C. The inner diameter of pusher 26 is designated by the letter D. The outer diameter of pusher 26 is designated by the letter E. The inner diameter of delivery catheter 20 is designated by the letter F, and the outer diameter of delivery catheter 20 is designated by the letter G.

The inner diameter A of particle 24 is preferably just larger than the outer diameter of wire 22. For the purpose of the present invention, an occlusion particle 24 is defined as having an outer diameter B smaller than the inner diameter F of delivery catheter 20, an inner diameter A larger than the outer diameter of wire 22, and a length C less than approximately 1 cm. In the preferred embodiment, outer diameter B of particle 24 is preferably less than 0.75 mm. In another preferred embodiment, outer diameter B of particle 24 is between 0.2 mm and 0.75 mm. Also, in the preferred embodiment, length C of particle 24 is less than approximately 1.2 mm. In another preferred embodiment, length C of particle 24 is between 0.7 mm and 1.2 mm.

The inner diameter D of pusher 26 is larger than the outer diameter of wire 22, but must be smaller than the outer diameter B of particle 24. The outer diameter E of pusher 26 must be smaller than the inner diameter F of delivery catheter 20. In the preferred embodiment, delivery catheter 20 has an outer diameter G of 0.7 mm and an inner diameter F of 0.53 mm. In addition, pusher 26 has an outer diameter E of 0.33 mm and an inner diameter D of 0.15 mm. However, while these are preferred embodiments, and while the remainder of system 18 must be sized accordingly, any suitable dimensions can be used. It is also preferred that the inner diameter A of particle 24 is less than 3 mm.

It should be noted that any suitable method of mounting particles 24 onto wire 22 can be used. For instance, a single unitary piece can be mounted onto wire 22 and cut, or divided, into discrete particles 24. In addition, the discrete particles 24 can first be formed and then mounted individually, or in groups, onto wire 22.

It should also be noted that while platinum is a preferred material for particles 24, other materials can be used. For instance, the present embolization system 18 can be used in conjunction with chemotherapeutic drugs. In that instance, it is beneficial to form particle 24 of radioisotope material which enhances the effectiveness of the chemotherapy, and which enhances the effectiveness of embolization on tumors. Also, the material of particle 24 can be a polymeric substance. Further, the density of the material used to form particle 24 will, in some instances, be determined based on the technique to be used. For example, the particles can be made of a material having a density greater than blood or less than blood, depending on the requirements for the particular vasculature being embolized.

The present invention overcomes certain problems associated with occlusions based on thrombus formation. If thrombus formation does form part of the occlusive effect of particles 24, and anti-coagulant therapy is used, the treating physician can easily release additional particles 24 to obtain desired occlusion. This can be carefully monitored and controlled so that substantially no reflux occurs.

The present invention also provides an efficient technique and apparatus for aligning particles 24 generally along a longitudinal axis of delivery catheter 20. Particles 24 cannot be released from wire 22 unless they are released at the distal end of wire 22, and then only when the treating physician advances pusher 26 to a sufficient extent to release the particles 24. This essentially precludes particles 24 from being dislodged within delivery catheter 20 at an undesirable position. Thus, delivery catheter 20 does not become blocked by particles 24 lodging against one another and the lumen walls of catheter 20.

It should also be noted that the J-shaped or hook-shaped distal end portion 38 of wire 22 allows the treating physician to release particles 24, but also helps to prevent intimal injury. Since the curved portion 38 is quite large and smoothly curved, it does not damage the interior surface of the vessel.

In addition, the controlled release of particles 24 accomplished by the present invention substantially reduces the incidence of reflux. Since the treating physician is capable of monitoring the precise amount of particles 24 released, that amount can be controlled and adjusted when distal flow is reduced due to partial occlusion of the vessel. This substantially eliminates problems associated with reflux.

Although the present invention has been described with reference to preferred embodiments, workers skilled in the art will recognize that changes may be made in form and detail without departing from the spirit and scope of the invention.

What is claimed is:

1. An embolization system for entering a vessel at an entry point and occluding a lumen of the vessel at an occlusion site, comprising:

a catheter having a lumen, the catheter being formed of a material suitable to follow the lumen of the vessel from the entry point to the occlusion site;

a first elongate member, insertable within the lumen of the catheter;

an occlusion particle having a receiving passageway therein for receiving the first elongate member so the first elongate member guides movement of the occlusion particle;

a pusher, slidable relative to the first elongate member within the lumen of the catheter to engage the occlusion particle and to move the occlusion particle relative to the first elongate member; and wherein the first elongate member comprises a retaining end portion for controllably retaining the occlusion particle on the first elongate member.

2. The embolization system of claim 1 wherein the first elongate member comprises a wire and wherein the retaining end portion comprises:

a curved portion of the wire located generally at the distal end of the wire.

3. The embolization system of claim 2 wherein the wire comprises:

a flexible shape memory material, the curved portion being flexible to release the occlusion particle and return to its curved shape.

4. The embolization system of claim 1 wherein the pusher comprises:

a second elongate member having a receiving passageway so the pusher is slidable along the first elongate member, the first elongate member moving relative to the pusher within the receiving passageway of the occlusion particle.

5. The embolization system of claim 4 wherein the first elongate member comprises a wire and wherein the pusher comprises:

a tube having a lumen, the lumen sized large enough to slidably receive the wire and sized smaller than an outer dimension of the occlusion particle.

6. The embolization system of claim 5 wherein the pusher has a distal end portion for engaging the occlusion particle and pushing the occlusion particle along the wire so that the occlusion particle slides relative to the wire, the wire passing through the wire receiving passageway in the occlusion particle.

7. The embolization system of claim 6 wherein the receiving passageway of the occlusion particle comprises a bore defined by the occlusion particle, the bore being large enough to slidably receive the wire.

8. The embolization system of claim 1 wherein the occlusion particle is formed of radiopaque material.

9. A method of occluding a site in a vessel, comprising:

accessing the site in the vessel with a catheter having a lumen;

advancing an elongate member through the lumen;

pushing a plurality of embolizing articles over the elongate member, through the lumen, to the site;

selectively releasing a desired amount of the articles from the elongate member proximate the site in the vessel; and wherein the elongate member is a wire having a curved end portion, and said selectively releasing step further comprises straightening the curved end portion to release the desired amount of articles and allowing the end portion to return to its curved shape to retain additional articles on the wire.

10. An embolization system for entering a vessel at an entry point and occluding a lumen of the vessel at an occlusion site, comprising:

a catheter having a lumen, the catheter being formed of a material suitable to follow the lumen of the vessel from the entry point to the occlusion site;

a first elongate member, insertable within the lumen of the catheter;

an occlusion particle having a receiving passageway therein for receiving the first elongate member so the first elongate member guides movement of the occlusion particle;

a pusher, slidable relative to the first elongate member within the lumen of the catheter to engage the occlusion particle and to move the occlusion particle relative to the first elongate member; and wherein the occlusion particle is formed of radiopaque and radioisotope materials.

* * * * *